US008363929B2

(12) United States Patent
Kojima et al.

(10) Patent No.: US 8,363,929 B2
(45) Date of Patent: Jan. 29, 2013

(54) SHAPE MEASUREMENT APPARATUS AND CALIBRATION METHOD

(75) Inventors: Takeshi Kojima, Kyoto (JP); Daisuke Mitsumoto, Nagaokakyo (JP); Yasuhiro Ohnishi, Kyotanabe (JP); Tuo Zhuang, Kizugawa (JP); Yasumoto Mori, Jyoyo (JP)

(73) Assignee: OMRON Corporation, Kyoto (JP)

( * ) Notice: Subject to any disclaimer, the term of this patent is extended or adjusted under 35 U.S.C. 154(b) by 80 days.

(21) Appl. No.: 13/088,704

(22) Filed: Apr. 18, 2011

(65) Prior Publication Data
US 2011/0262007 A1 Oct. 27, 2011

(30) Foreign Application Priority Data

Apr. 26, 2010 (JP) ................. 2010-100994

(51) Int. Cl.
*G06K 9/00* (2006.01)
*G06K 9/46* (2006.01)
(52) U.S. Cl. .............. 382/154; 382/203; 348/135
(58) Field of Classification Search .......... None
See application file for complete search history.

(56) References Cited

U.S. PATENT DOCUMENTS

| 4,884,225 | A | * | 11/1989 | Fogarty et al. ............ 382/133 |
| 5,243,665 | A | * | 9/1993 | Maney et al. ............ 382/152 |
| 5,495,429 | A | * | 2/1996 | Craven et al. ............ 702/127 |
| 5,671,157 | A | * | 9/1997 | Saito ............ 345/419 |
| 5,675,377 | A | * | 10/1997 | Gibas ............ 348/47 |
| 5,864,640 | A | * | 1/1999 | Miramonti et al. ............ 382/312 |
| 6,064,759 | A | * | 5/2000 | Buckley et al. ............ 382/154 |
| 6,631,364 | B1 | * | 10/2003 | Rioux et al. ............ 1/1 |
| 6,721,444 | B1 | * | 4/2004 | Gu et al. ............ 382/154 |

(Continued)

FOREIGN PATENT DOCUMENTS
JP 5-296745 11/1993
(Continued)

OTHER PUBLICATIONS

Robert J. Woodham, "Gradient and curvature from the photometric-stereo method, including local confidence estimation", Journal of the Optical Society of America A, vol. 11, No. 11, XP55004116, Nov. 1, 1994, pp. 3050.

(Continued)

*Primary Examiner* — Manav Seth
(74) *Attorney, Agent, or Firm* — Greenblum & Bernstein P.L.C.

(57) ABSTRACT

The shape measurement apparatus calculates a characteristic amount for a plurality of points of interest on a surface of a measurement target object, based on an image obtained by image capturing with a camera, calculates an orientation of a normal line based on a value of the characteristic amount by referencing data stored in advance in a storage device, and restores the three-dimensional shape of the surface of the measurement target object based on a result of the calculation. The storage device stores a plurality of data sets generated respectively for a plurality of reference positions arranged in a field of view of the camera, and the data set to be referenced is switched depending on a position of a point of interest.

11 Claims, 17 Drawing Sheets

U.S. PATENT DOCUMENTS

| | | | |
|---|---|---|---|
| 7,016,527 B2 * | 3/2006 | Fujiwara | 382/154 |
| 7,251,347 B2 * | 7/2007 | Smith | 382/108 |
| 7,486,816 B2 * | 2/2009 | Aizawa et al. | 382/154 |
| 7,822,263 B1 * | 10/2010 | Prokoski | 382/152 |
| 2005/0180623 A1 | 8/2005 | Mueller et al. | |

FOREIGN PATENT DOCUMENTS

| | | |
|---|---|---|
| JP | 8-014849 | 1/1996 |
| JP | 08-14849 A | 1/1996 |
| JP | 9-280826 | 10/1997 |
| JP | 2005-321278 | 11/2005 |
| JP | 2006-047290 | 2/2006 |
| JP | 2008-216228 | 9/2008 |
| JP | 2009-168582 | 7/2009 |
| JP | 2009-168582 A | 7/2009 |
| JP | 2009-273655 A | 11/2009 |

OTHER PUBLICATIONS

Hertzmann A et al., "Example-Based Photometric Stereo: Shape Reconstruction with General, Varying BRDFs", IEEE Transactions on Pattern Analysis and Machine Intelligence, IEEE Service Center, Los Alamitos, CA, US, vol. 27, No. 8, XP011135149, Aug. 1, 2005, pp. 1254-1264.

Search report from E.P.O., mail date is Aug. 19, 2011.

Japan Office action, mail date is Sep. 4, 2012.

* cited by examiner 255                                                          0

255　　　　　　　　　　　　　　　　　　　　0

SHAPE MEASUREMENT APPARATUS AND CALIBRATION METHOD

CROSS REFERENCE TO RELATED APPLICATIONS

This application claims priority to Japanese Patent Application No. 2010-100994, filed Apr. 26, 2010, the disclosure of which is expressly incorporated by reference herein in its entirety.

BACKGROUND OF THE INVENTION

1. Technical Field

The present invention relates to a technique for measuring a three-dimensional shape of a surface of a measurement target object.

2. Related Art

A technique is known in which an image captured by a camera is analyzed to obtain a normal line (or gradient) on a surface of a measurement target object, thereby restoring the three-dimensional shape of the surface. For example, Patent Document 1 discloses a method for measuring the gradient of a solder surface by emitting a concentric pattern of light from ring illuminators disposed in multiple stages. Also, Patent Document 2 discloses a method for restoring the shape of the surface of a body tissue by irradiating a light pattern onto the body tissue with a medical endoscope, and calculating a normal line based on the specular direction of the light. Also, Patent Document 3 discloses a method for measuring the gradient of a solder surface after the reflow process by using parallel light illumination and a line sensor. Other than those, methods are known such as a method in which a normal line on the surface of an object is obtained by sequentially turning on a plurality of light sources and observing changes in shadows in the object (so-called a photometric stereo method), a method in which the orientation of a normal line to the surface of an object is obtained by irradiating the object surface with three colors of light, namely, red light, blue light and green light, at different angles, and observing the color of the object surface (structured-light method).

RELATED ART DOCUMENTS

Patent Documents

[Patent Document 1] Japanese Published Patent Application No. H8-14849
[Patent Document 2] Japanese Published Patent Application No. 2009-273655
[Patent Document 3] Japanese Published Patent Application No. 2009-168582

As described above, although there are various approaches to shape measurement methods based on normal line calculation, they share the common basic principle that characteristic amounts (colors, brightness and the like) of an image and normal lines (or light source angles) are associated with each other. Taking a measurement apparatus for a specular object as an example, as in FIG. 17A, when characteristics (color, brightness and the like) of incident light from a light source L are observed at a certain measurement point P, an angle $\theta$ of the normal line at the point P is obtained as ½ of the angle of the light source L.

With this type of apparatus, generally, the angle $\theta$ of the light source L is set by setting the center of the field of view of a camera as a reference position. Therefore, in a strict sense, when a measurement point (pixel position) is removed from the center of the field of view, an error occurs in the normal line calculation. For example, as shown in FIG. 17B, although an actual angle $\theta'$ of the normal line at a measurement point P' is larger than the angle $\theta$ of the normal line at the center point P, both angles are calculated as the same angles. Here, the error that occurs ($|\theta'-\theta|$) depends on the distance d from the center point P in the field of view to the measurement point P' and the distance l from the field center point P to the light source L, and the error increases as the distance d increases and the error decreases as the distance l increases. Conventionally, errors have been ignored in practice by designing the apparatus such that the distance l is much greater than the distance d.

However, in the field of automated optical inspection (AOI systems) of circuit boards or the like, due to a need for reducing the size of inspection apparatuses, or achieving a wider field of view for improved inspection cycles, it is difficult to provide a sufficient difference between the distance d and the distance l. Accordingly, the degree of an error in the normal line calculation cannot be ignored.

SUMMARY

The present invention has been achieved in view of the above issues, and an object thereof is to provide a technique for reducing, as much as possible, an error in the normal line calculation due to a positional difference between measurement points, and calculating the three-dimensional shape of a measurement target object accurately.

In order to achieve the above-described object, with the present invention, the calculation error can be suppressed to the extent that it is practically ignorable, by appropriately switching data (such as tables, conversion expressions or the like) used in normal line calculation depending on the position of the measurement point (point of interest).

Specifically, the present invention provides a shape measurement apparatus including an illumination unit (i.e., illuminator) that irradiates light onto a measurement target object disposed on a stage, an image capturing unit that captures an image of the measurement target object, a characteristic amount calculation unit that calculates a characteristic amount relating to a color or brightness of a plurality of points of interest on a surface of the measurement target object, based on an image obtained by image capturing with the image capturing unit in a state in which light is emitted from the illumination unit, a storage unit that stores in advance data associating a value of the characteristic amount with information for specifying an orientation of a normal line on the surface based on the characteristic amount value, and a shape calculation unit that calculates orientations of normal lines at the plurality of points of interest based on the values of the characteristic amount calculated by the characteristic amount calculation unit by referencing the data stored in the storage unit, and calculates a three-dimensional shape of the surface of the measurement target object based on a result of the calculation, wherein the storage unit stores a plurality of data sets generated respectively for a plurality of reference positions arranged in a field of view of the image capturing unit, and the shape calculation unit switches the data set to be referenced depending on a position of a point of interest.

With this configuration, since data is switched depending on the position of the point of interest, an error in the normal line calculation can be sufficiently suppressed regardless of the position of the point of interest. Accordingly, compared with conventional apparatuses, it becomes possible to accurately obtain a three-dimensional shape of the surface of the measurement target object. Conversely, it is possible to achieve size reduction, and a wider field of view of the apparatus while maintaining the same level of accuracy as conventional apparatuses. Here, for example, a normal line orientation, gradient (inclination), or incident light (light source) angle corresponds to "information for specifying an orientation of a normal line on the surface based on a value of the characteristic amount".

It is preferable that the field of view of the image capturing unit is divided into a plurality of sub-regions such that each sub-region includes a reference position, each sub-region is associated with one data set, and the shape calculation unit selects the data set that corresponds to a sub-region to which the point of interest belongs, as the data set to be referenced. With this configuration, the data to be referenced can be determined easily, and thus simplification and faster processing can be achieved. Of course, the method for selecting data is not limited thereto. Although the processing becomes a little complicated, it is possible to calculate a normal line by detecting a reference position that is closest to the point of interest, and referencing data corresponding to the reference position, or alternatively, by selecting a plurality of reference positions close to the point of interest, and using the plurality of data sets corresponding to the reference positions (e.g., by performing interpolation).

It is preferable that each of the plurality of data sets is generated by using an image of a model object whose surface shape is known, the image being obtained by disposing the model object at the reference position and image capturing with the image capturing unit in a state in which light is emitted from the illumination unit. By generating data by using the apparatus itself, individual differences, assembly errors or the like in the illumination unit or the image capturing unit can be reflected in the data, and thus improved accuracy can be expected.

It is preferable that the illumination unit is a surface light source that has a light emission region having a predetermined area, and the spectral distributions of light that is emitted from different positions in the light emission region are mutually different. By using such an illumination unit, it is possible to obtain the three-dimensional shape of the measurement target object by a single measurement (illumination and image capturing), and the measurement time can be shortened.

It is preferable that the illumination unit is a surface light source that emits light formed by mutually overlaying a plurality of illumination patterns that have mutually different emission intensity distributions, or that sequentially emits said plurality of illumination patterns, the emission intensity distribution of each illumination pattern being set such that the emission intensity varies linearly with respect to an angle around a central axis given by a predetermined straight line that passes through a point at which the measurement target object is disposed and is parallel to the stage. By using such an illumination unit, accurate measurement is possible even for an object having uneven reflection characteristics or an object having a rough surface. Note that there may be a case in which it is difficult to realize strict linearity due to structure, design or other reasons. In such a case, it is sufficient if linearity is substantially realized. That is, in the present invention, the phrase "the emission intensity varies linearly" is a concept that includes a state in which "the emission intensity varies substantially linearly".

Note that the present invention can be understood as a shape measurement apparatus that includes at least some of the above-mentioned units. The present invention can also be understood as a calibration method for such a shape measurement apparatus, or a shape measurement method that includes at least some of the processing or a program for realizing that method. Each of the units and the processing may be combined as much as possible to realize the invention.

For example, a calibration method of the present invention is a calibration method of a shape measurement apparatus that irradiates light onto a measurement target object with an illumination device, captures an image of the measurement target object by an image capturing device in a state in which light is emitted, and calculates a three-dimensional shape of a surface of the measurement target object based on a characteristic amount relating to a color or brightness obtained for a plurality of points of interest on the surface of the measurement target object in the captured image, the calibration method including the steps of disposing an object whose surface inclination is known in a field of view of the image capturing device, irradiating with the illumination device the object with light from at least a plurality of different directions, the emission intensity distributions of the light from the different directions being mutually different, extracting a characteristic amount with respect to an inclination of the surface of the object based on the captured image, and storing data associating a position on the image at which the object is disposed with the extracted characteristic amount as data for calibration of measurement values at a plurality of measurement positions of the measurement target object. Here, "object whose inclination is known" is preferably a hemispherical body. This is because normal line information for all directions (360 degrees) can be obtained by a single image capturing step, and a normal vector can be easily calculated with a formula for a sphere.

With the present invention, an error in the normal line calculation caused by the positional difference between measurement points can be suppressed as much as possible, and the three-dimensional shape of the measurement target object can be accurately calculated.

DETAILED DESCRIPTION

Hereinafter, preferred embodiments of the present invention will be described in detail with reference to the drawings. A shape measurement apparatus of the present embodiment performs three-dimensional measurement of a specular object by performing image analysis. The apparatus can be applied to object recognition in various types of automatic measurement apparatuses, automatic inspection apparatuses, robotic vision, and the like, and preferably applied to, for example, soldering quality inspection in an automatic optical inspection apparatus (AOI system) for circuit boards, recess/protrusion inspection on the surface of metal-processed objects, and the like.

Overall Configuration of Measurement Apparatus

Figure 1:
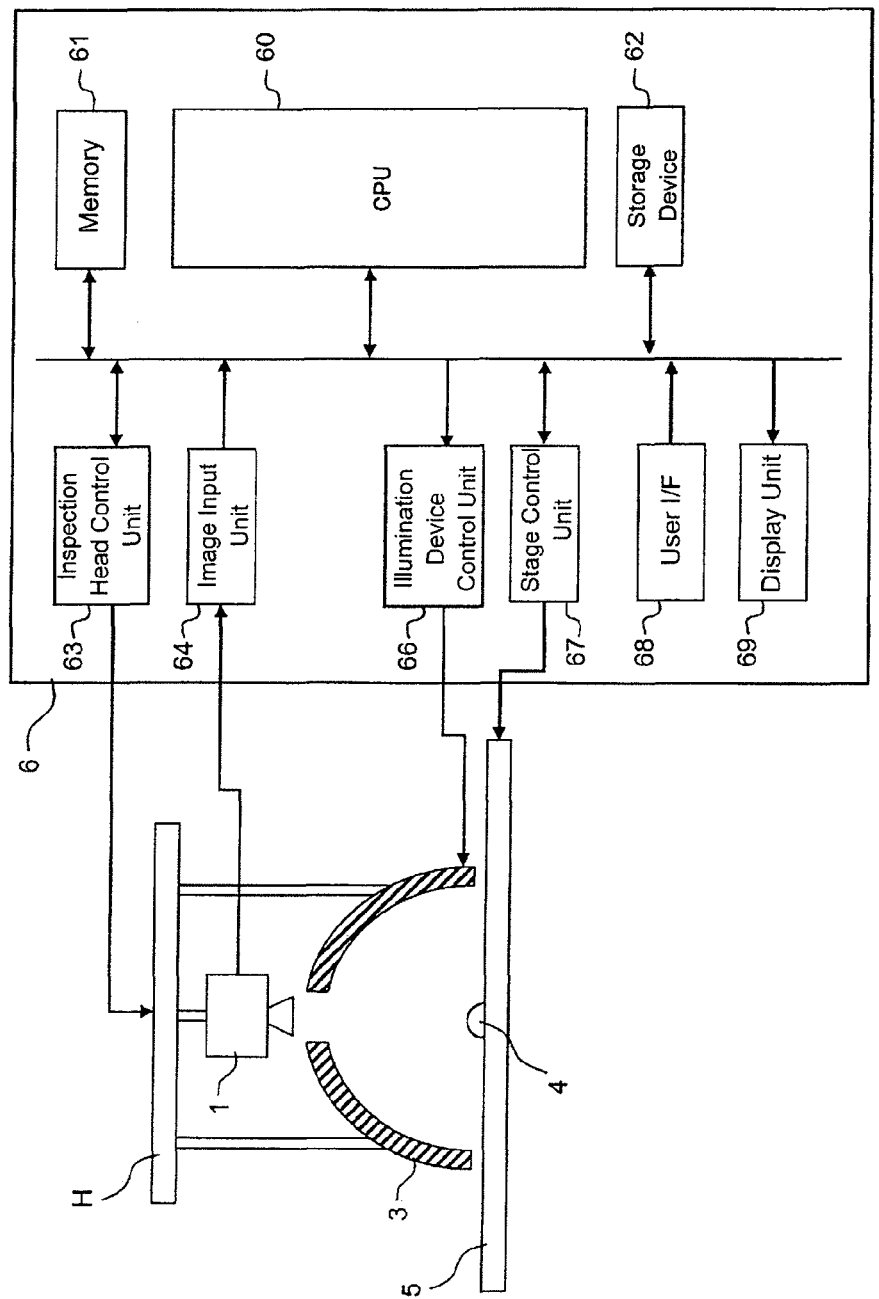
FIG. 1 is a diagram schematically illustrating the hardware configuration of a shape measurement apparatus.

The overall configuration of a shape measurement apparatus is described with reference to FIG. 1. FIG. 1 is a diagram schematically illustrating the hardware configuration of the shape measurement apparatus.

Generally, the shape measurement apparatus is provided with a measurement stage 5, an inspection head H and an information processing apparatus 6. An illumination device 3 for emitting measurement light onto a measurement target object 4 disposed on the measurement stage 5, and a camera (image sensor) 1 for capturing an image of the measurement target object 4 from above in the vertical direction are attached to the inspection head H. The information processing apparatus 6 includes a CPU (central processing unit) 60, a memory 61, a storage device 62, an inspection head control unit 63, an image input unit 64, an illumination device control unit 66, a stage control unit 67, a user interface (I/F) 68, a display unit 69 and the like. The inspection head control unit 63 has the function of controlling movement of the inspection head H in a Z direction (direction orthogonal to the measurement stage 5), and the stage control unit 67 has the function of controlling movement of the measurement stage 5 in an X direction and a Y direction. The illumination device control unit 66 has the function of turning on/off the illumination device 3 (switching illumination patterns as required). The image input unit 64 has the function of loading digital images from the camera 1. The user I/F 68 is an input device operated by the user, and a pointing device, a touch panel, a keyboard or the like may be used as the user I/F 68, for example. The display unit 69 is where measurement results or the like are displayed on a screen, and is configured from a liquid crystal display, for example.

At the time of measurement, the inspection head H and the measurement stage 5 move relative to each other, and the measurement target object 4 is positioned at a predetermined measurement position (in the example of FIG. 1, at the center of the illumination device 3 (intersection point of the optical axis of the camera 1 and the measurement stage 5)). Then, an image is captured while measurement light is emitted from the illumination device 3. The image captured by the camera 1 is loaded by the information processing apparatus 6 via the image input unit 64, and provided for the use in image analysis to be described later. The configuration of and processing performed by the shape measurement apparatus will be described in detail below.

Illumination Device

The illumination device 3 is a surface light source having a dome shape as shown in FIG. 1, and the entirety of this dome shape serves as a light emission region. Note that an opening is provided at a zenith portion of the illumination device 3 for the camera 1. The illumination device 3 can be configured from, for example, a dome-shaped color filter and a light source that emits white light from the outer side of the color filter. Also, a configuration may be adopted, for example, in which a plurality of LED chips are arrayed inside the dome, and light is emitted onto the LED chips through a diffuser plate. Also, the illumination device 3 may be configured by forming a liquid crystal display, an organic EL display or the like in a dome shape.

It is preferable that the light emission region of the illumination device 3 has a hemispherical dome shape such that light irradiation can be performed from all directions of the measurement target object 4. In this manner, it is possible to measure normal lines in every direction. However, the light emission region may have any shape as long as light irradiation from the position that corresponds to the direction of the normal line to be measured is possible. For example, if the orientation of the normal lines on the surface is substantially limited to the vertical direction, it is not necessary to perform light irradiation from a horizontal direction (shallow angle direction).

Figure 2:
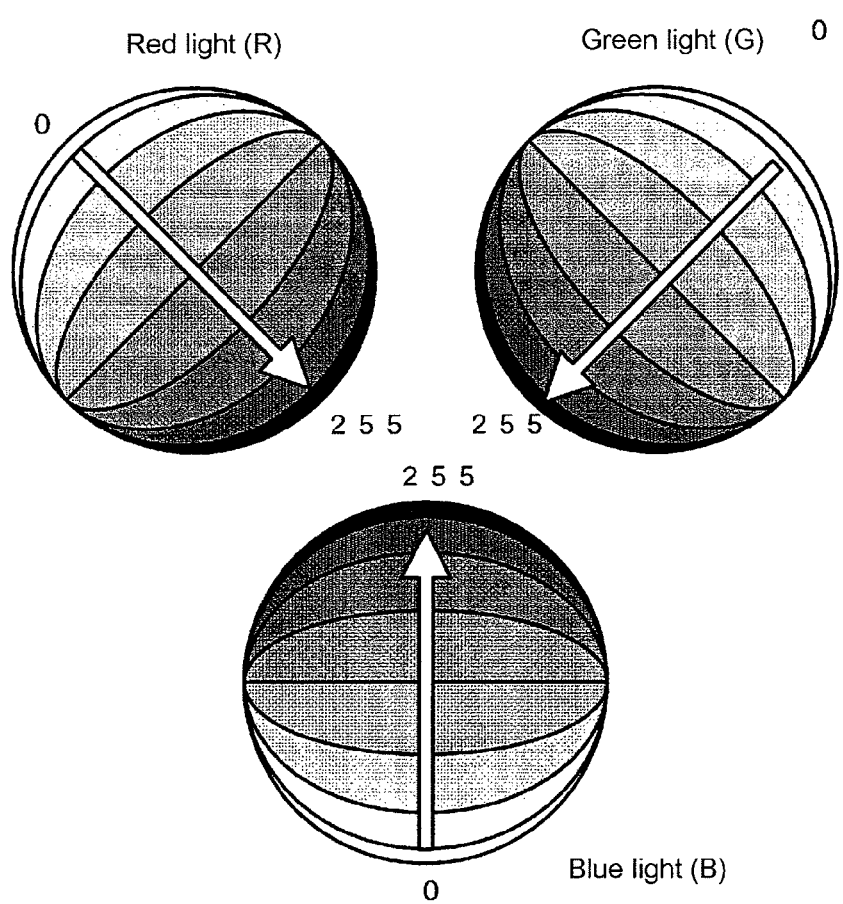
FIG. 2 is a diagram illustrating color patterns in a light emission region of the illumination device, for each of red, green and blue.

Light emission at various positions in the light emission region of the illumination device 3 is set such that the spectral distributions of light that is emitted from different positions are mutually different. For example, when light emission is realized by a combination of three colors of light components, namely, red light (R), green light (G) and blue light (B), the emission intensities of the RGB components may be varied on the dome in mutually different directions, as shown in FIG. 2. Here, the variation directions of the RGB components are set to define angles of 120 degrees. Due to the combination of the RGB components as described above, the light emitted at different positions in the light emission region has mutually different combinations of RGB components. Accordingly, it is possible to perform settings such that light with mutually different spectral distributions is emitted from different positions, and the spectral distributions of the incident light (RGB intensity ratio) are different for different incident directions on the measurement target object 4. Note that the emission colors are not limited to the three colors described above, and three or more colors of color components (color channels) may also be used.

Figure 3A:
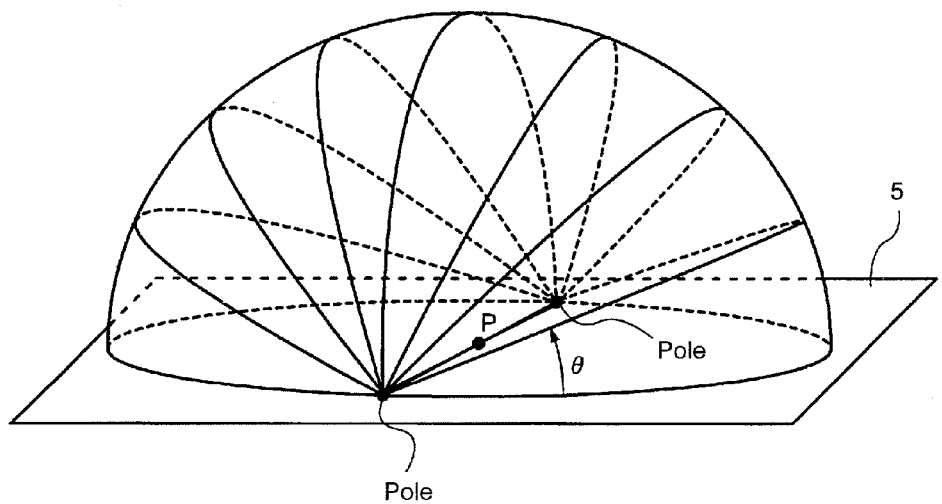
FIGS. 3A and 3B are diagrams illustrating variation of each of the RGB colors in the light emission region of the illumination device, FIG. 3A being a perspective view, and FIG. 3B being a side view.
Figure 3B:
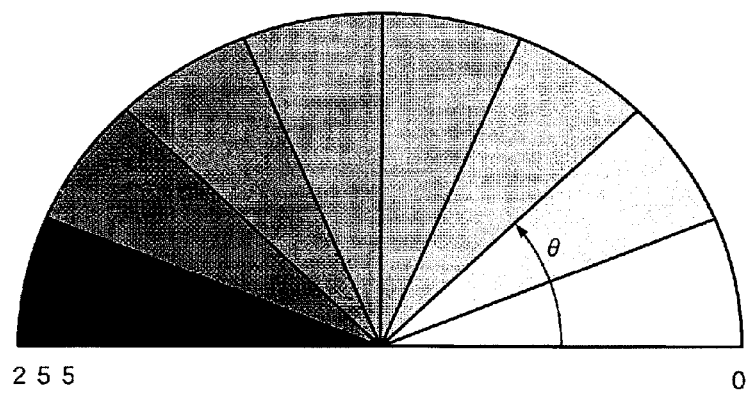

FIGS. 3A and 3B show intensity variation (illumination pattern) of one light component shown in FIG. 2. FIG. 3A is a perspective view illustrating isochromatic (equal emission intensity) lines of one light component. FIG. 3B is a side view corresponding to FIG. 3A. In this manner, an intersection line of the plane passing through the diameter of the dome (hemisphere) and the dome forms an isochromatic line. Note that although in FIGS. 2 and 3 the emission intensities of the RGB components are shown as varying stepwise (in eight steps in the figures), this is for the sake of simplicity of the drawings, and actually, the emission intensity (luminance) of each light component varies continuously. The emission intensity is set so as to vary linearly with respect to the angle. More specifically, when a minimum value of the emission intensity is set to Lmin, a maximum value of the emission intensity is set to Lmax, and the angle formed by the plane including an isochromatic line and the horizontal plane (measurement stage 5) is set to θ, the emission intensity L(θ) on the isochromatic line is set so as to satisfy the relation, L(θ)=Lmin+(Lmax−Lmin)× (θ/π). When the "poles" are defined as shown in FIG. 3A, this angle θ represents the longitude, and it is possible to state that the light source distribution (illumination pattern) in the present embodiment varies linearly with respect to the longitude. Alternatively, it is also possible to state that the illumination pattern is set such that by taking a straight line that passes through a point O at which the measurement target object is disposed, and is parallel to the measurement stage 5 as a central axis, the emission intensity varies linearly with respect to the angle θ around this central axis.

Figure 4:
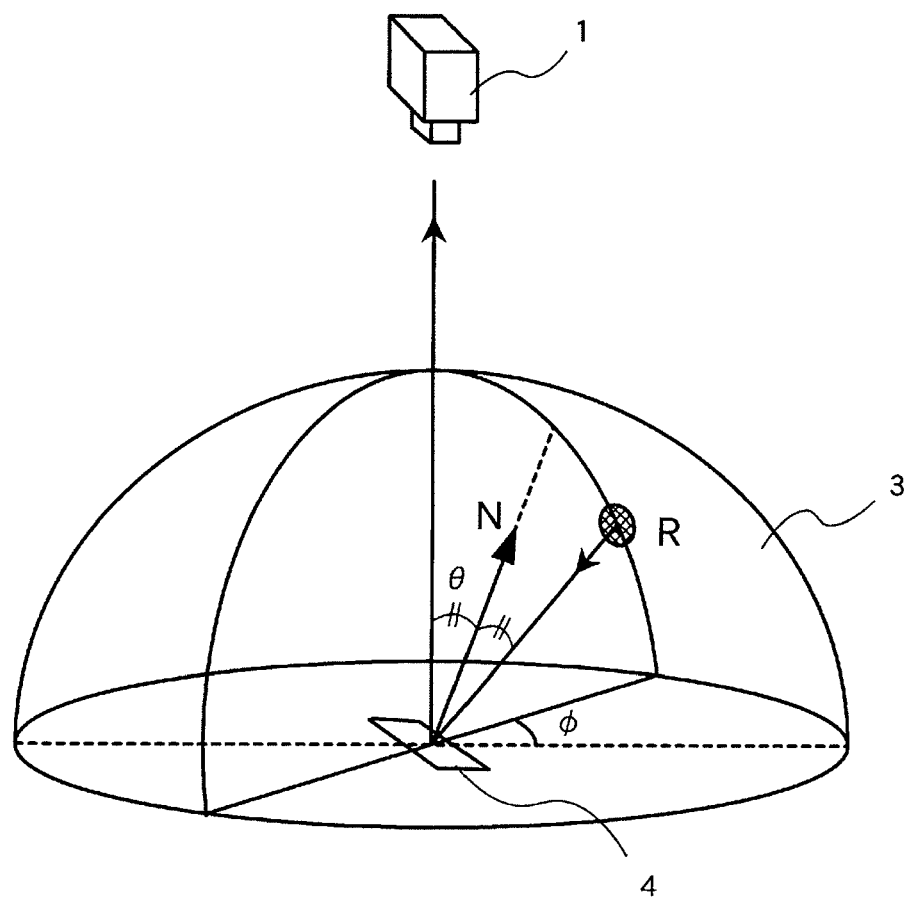
FIG. 4 is a diagram illustrating the correspondence between the orientation of a normal line on the surface of a measurement target object and the light emission region.

By using an illumination device having the light source distribution (illumination pattern) as described above, it is possible to measure the surface shape (orientations of normal lines) of the measurement target object based on a single image. This will be described with reference with FIG. 4. The orientation of the normal line at a certain point on the surface of the measurement target object 4 is an arrow N, its zenith angle is θ, and its azimuth angle is φ. The color at the certain point captured by the camera 1 is given by the reflection light of the light that is emitted at a region R of the illumination device 3 and incident on the measurement target object 4. In this manner, the orientation of the normal line on the surface (θ, φ) and the light source direction (the position in the light emission region of the illumination device 3) correspond to each other on a one-to-one basis. Since light incident from different directions have different spectral distributions (the spectral distributions of light emitted from different positions in the light emission region are mutually different), it is possible to calculate the orientation of the normal line at a target point from the zenith angle and the azimuth angle, by examining the color of the captured image (spectral distribution).

Table

In this manner, the color, brightness and the like of a pixel corresponds to the orientation of the normal line at the corresponding point or the light source angle on a one-to-one basis. Accordingly, in the shape measurement apparatus, a table in which the characteristic amount values relating to the color, brightness and the like of pixels are associated with light source angles is created in advance, and registered in the storage device 62. In the present embodiment, since the illumination device 3 projects light formed by combining three light components, namely, red light (R), green light (G) and blue light (B), the ratio among the RGB components is used as the characteristic amount. For example, the (R, G, B) combination can be used as the characteristic amount by performing normalization with respect to the RGB components with the largest luminance being set to 1. Also, the ratio of other colors with respect to a certain color (here, G), for example, R/(R+G), B/(B+G), or the like may be used as the characteristic amount.

Figure 17A:
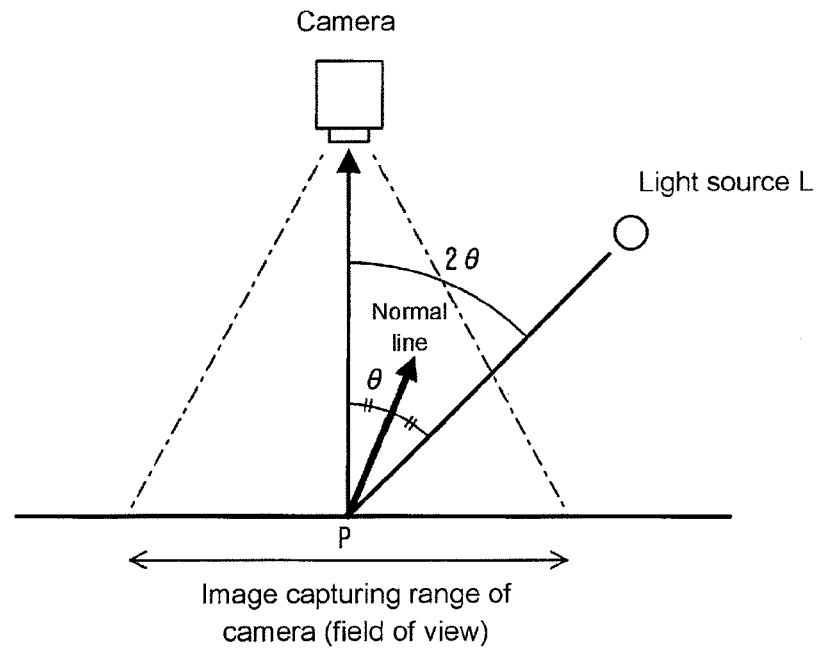
FIG. 17 is a diagram for describing a calculation error due to a positional difference between measurement positions.
Figure 17B:
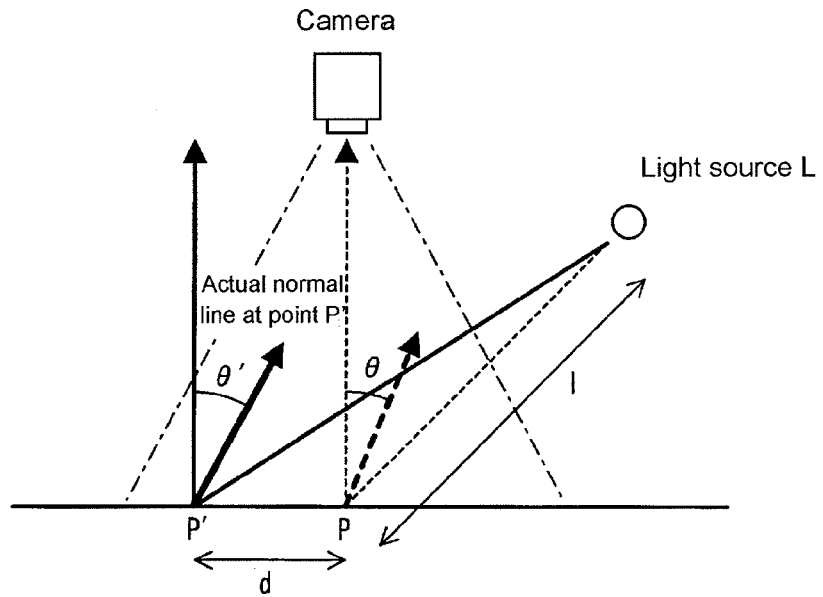

Incidentally, when the normal line orientation is calculated by using such a table, as described with reference to FIG. 17B, an error due to a positional difference between the measurement points may be a problem. Therefore, in the shape measurement apparatus of the present embodiment, a plurality of reference positions are set in the field of view of the camera 1, and different tables are prepared for each of the reference positions. Then, the error is suppressed as much as possible by calculating the normal line by selecting a table appropriate for a target position.

Figure 5:
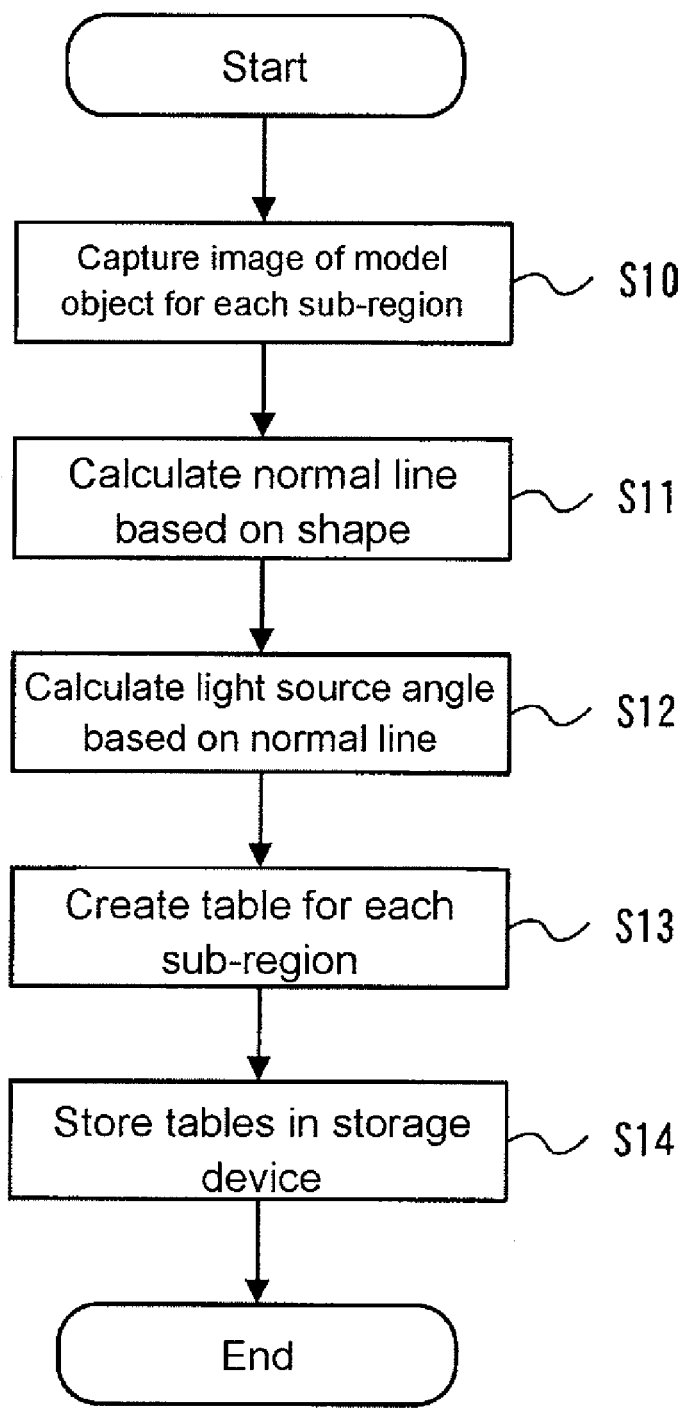
FIG. 5 is a flowchart illustrating the flow of table creation processing.
Figure 6A:
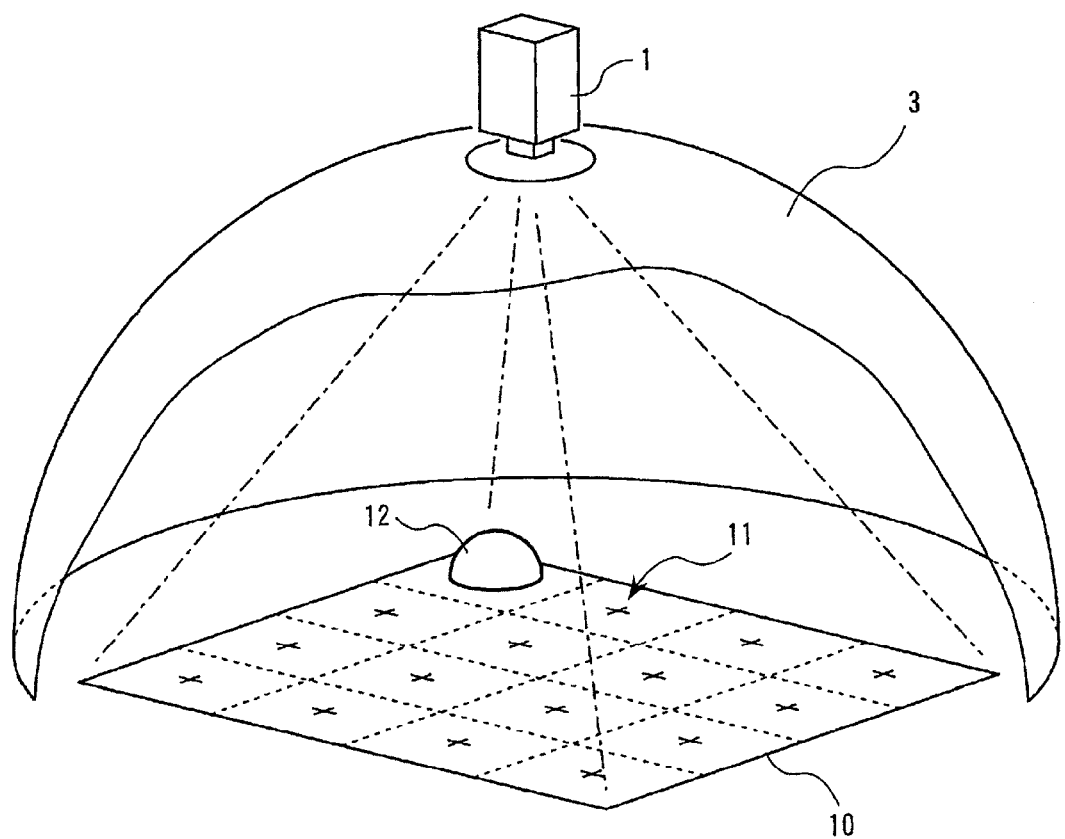
FIG. 6A is a perspective view of a state when a table creation image is captured.
Figure 6B:
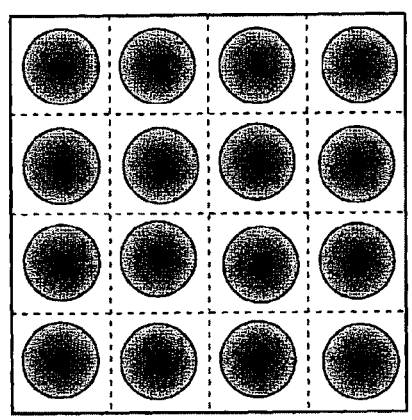
FIG. 6B is a diagram illustrating an example of the table creation image.

With reference to FIGS. 5 and 6, table creation processing will be described in detail below. FIG. 5 is a flowchart illustrating the flow of the table creation processing. FIG. 6A is a perspective view illustrating the state when the table creation image is captured (the view illustrates the illumination device 3 with a portion thereof being cut off). FIG. 6B is a diagram illustrating an example of the table creation image. Note that the processing shown in FIG. 5 is realized by the CPU 60 of the information processing apparatus 6 loading a program from the storage device 62, and executing the program. Note that part or the entirety of these functional blocks may be configured by an ASIC, PLD (programmable logic device), or the like.

As shown in FIG. 6A, a field of view 10 of the camera 1 is virtually divided into sixteen (4×4) sub-regions, and a reference position 11 is set at the center of each sub-region. Then, a model object 12 whose surface shape is known (a hemispherical body is used here) is disposed aligned with one of the reference positions 11, the illumination device 3 irradiates the model object 12 with light, and the camera 1 performs image capturing (step S10). The captured image is loaded by the information processing apparatus 6 via the image input unit 64. The processing is repeated while the position of the model object 12 is changed, thereby obtaining sixteen images corresponding to the reference positions (the sub-regions). FIG. 6B is an image obtained by merging the sixteen images. Note that since the precise position and size of the model object 12 are obtained based on the images in the next step, strict positioning of the model object 12 is not necessary at the time of capturing an image thereof.

Next, the CPU 60 analyzes the images, obtains the central coordinates and the diameter of the model object 12 in the sub-regions, and calculates the angle of the normal line of each pixel with a formula for a sphere by using the central coordinates and the diameter (step S11). Next, the CPU 60 converts the angle of the normal line of each pixel into the light source angle (step S12). At this time, although the light source angle may be obtained by simply doubling the zenith angle of the normal line, preferably, a geometrical/optical correction calculation is performed so as to obtain the light source angle when viewed from the reference position 11.

Next, the CPU 60 obtains a characteristic amount value of each pixel for each sub-region, and creates a table in which the characteristic amount values are associated with the light source angles (step S13). Sixteen tables created in this manner are stored in the storage device 62 (step S14).

Note that although it is possible to use a table (general-purpose table) created by another shape measurement apparatus, preferably, the tables are created by using the shape measurement apparatus itself. By doing so, individual differences, assembly errors and the like of the illumination device 3 and the camera 1 can be reflected in the tables, and thus a higher accuracy can be expected in comparison with calculation using the general-purpose table. The table creation processing is preferably performed when the apparatus is shipped. Furthermore, if aging degradation occurs in the illumination device 3 or the camera 1, the tables may be updated (calibrated) on a regular basis.

The model object 12 may have any shape. For example, a polyhedron may be used, or a plate whose shape is known may be inclined or rotated at various angles. Note that in order to reduce the number of times of image capturing so as to reduce work for creating tables, it is preferable to use an object whose surface shape includes as many normal line (gradient) components as possible. A spherical body (if the image capturing direction is one direction, an hemisphere may be used as in the present embodiment) is optimal as the model object 12 since it is possible to obtain normal line information for all directions in a single image capturing step, and to easily calculate normal vectors with a formula for a sphere.

Note that although sixteen (4×4) sub-regions are provided in the present embodiment, the division number of the region, and the arrangement of the reference positions are not limited thereto, and may be appropriately designed according to the range of the field of view of the camera 1, required accuracy, and the like. Also, instead of creating tables at one time after capturing images of all sub-regions, image capturing and table creation may be performed for each sub-region.

Shape Measurement

Figure 7:
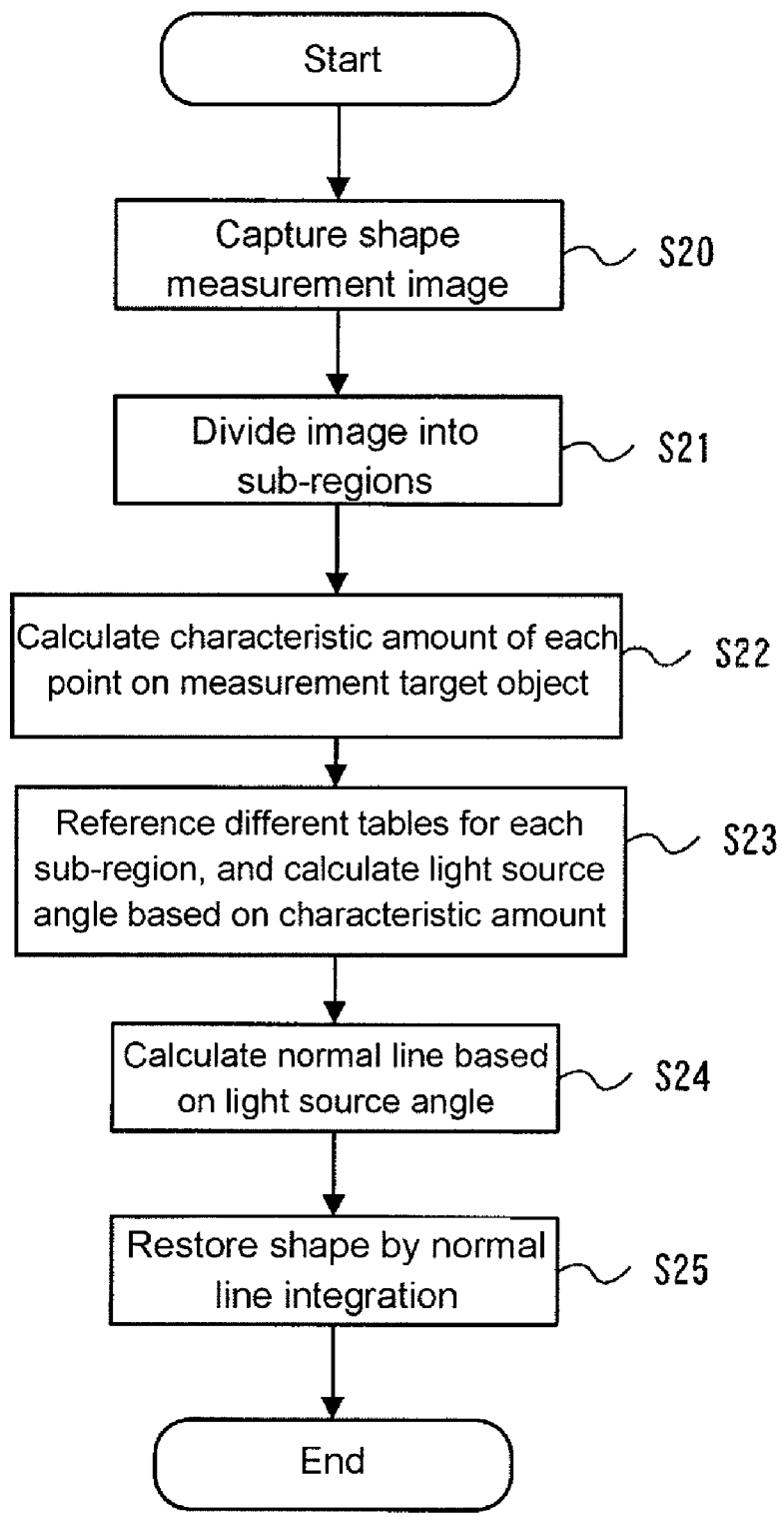
FIG. 7 is a flowchart illustrating the flow of shape measurement processing.

Next, with reference to FIG. 7, the functions and the processing flow relating to shape measurement will be described. FIG. 7 is a flowchart illustrating the flow of the shape measurement processing. Although these processes are realized by the CPU 60 of the information processing apparatus 6 loading a program from the storage device 62 and executing the program, part or the entirety thereof may be configured by an ASIC, PLD (programmable logic device), or the like.

When a measurement target object is positioned at a predetermined measurement position, the CPU 60 irradiates the measurement target object with light from the illumination device 3, and performs image capturing with the camera 1 (step S20). The captured image is loaded via the image input unit 64. Next, the CPU 60 divides the image into sixteen sub-regions (step S21), and calculates the above-described characteristic amount value for each pixel (point of interest) corresponding to the measurement target object (step S22).

When the CPU 60 reads in a table corresponding to the first sub-region from the storage device 62, the CPU 60 references the table, and converts the characteristic amount of each point of interest that belongs to the first sub-region into the light source angle. When calculation for the first sub-region is finished, the CPU 60 reads in a table corresponding to the second sub-region, and obtains the light source angles of the points of interest that belong to the second sub-region. In this manner, tables to be referenced are appropriately switched for each sub-region (that is, depending on the position of the point of interest), and the light source angle is calculated for all points of interest (step S23).

Figure 8A:
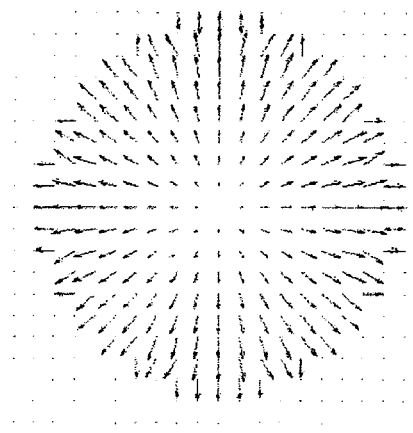
FIG. 8A is a diagram illustrating an example of a normal line map.

Subsequently, the CPU 60 calculates the orientations of normal lines based on the light source angles of the points of interest (step S24). An example of the normal line map calculated based on the image of the hemispherical measurement target object 4 is shown in FIG. 8A. Note that the normal line map is a map in which normal lines at the respective points on the surface of the measurement target object are shown as unit vectors.

Figure 8B:
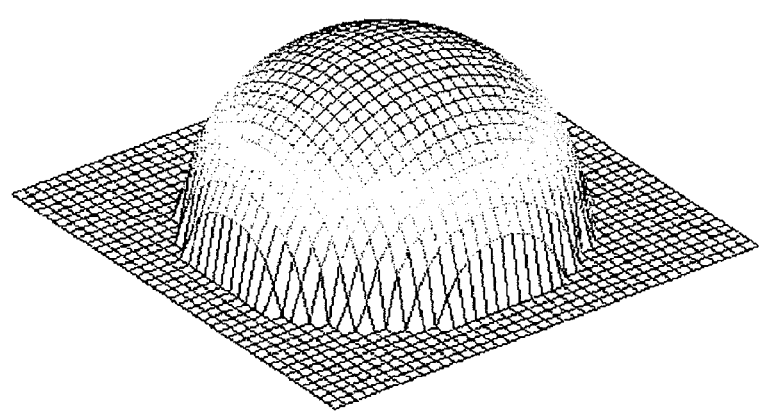
FIG. 8B is a diagram illustrating an example of a restored shape.

Lastly, the CPU 60 converts the normal line at each point of interest obtained in step S24 into a gradient, and restores the three-dimensional shape of the measurement target object by connecting the gradients (step S25). Such processing is referred to here as "integration". The shape restored based on the normal line map in FIG. 8A is shown in FIG. 8B.

With this method, it is possible to accurately restore the three-dimensional shape of the surface of the measurement target object. Note that although the normal line is calculated by using tables in the present embodiment, the normal line can be calculated with, for example, a conversion expression (approximation expression) in which the normal line orientation is calculated from characteristic amount values, instead of by using tables. In such a case, the parameter value of the conversion expression is set for each sub-region, and the parameter values may be switched depending on the position of the point of interest targeted for image capturing performed by a camera.

Advantage of Embodiment

According to the shape measurement apparatus of the present embodiment, tables are switched depending on the position of the point of interest, and thus the error in the normal line calculation can be made sufficiently small regardless of the position of the point of interest. Accordingly, in comparison with conventional apparatuses, it is possible to accurately obtain the three-dimensional shape of the surface of the measurement target object. Putting it another way, it becomes possible to reduce the size or achieve a wider field of view of the apparatus, while keeping the same level of accuracy as in conventional apparatuses. Also, since each sub-region is associated with a table, and a table to be referenced is switched depending on the sub-region to which the point of interest belongs, the table to be referenced can be easily determined, thereby achieving simplification and faster processing.

Also, since an illumination device 3 with which the spectral distribution of the incident light is mutually different for all incident angle directions is used as an illumination for the shape measurement, it is possible to obtain the normal line orientations of the measurement target object 4 for both the zenith angle component and the azimuth angle component based on a single image. Since an image needs to be captured only once, and the normal line orientation can be calculated simply by checking the table in which the correspondence relationship between the normal lines and the characteristic amounts is stored, it is possible to measure the surface shape of the measurement target object 4 easily (in a short time).

Figure 9:
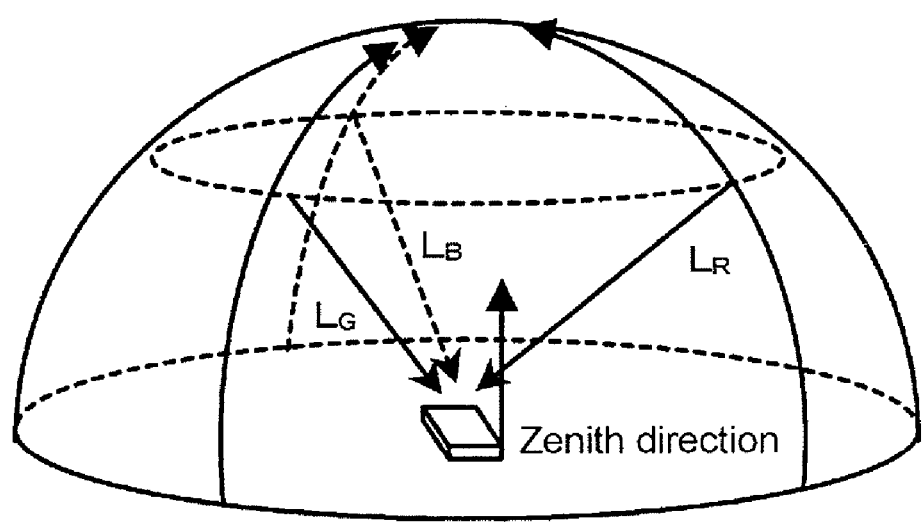
FIG. 9 is a diagram illustrating an effect by the color pattern of the illumination device.

In the case of capturing an image of a diffusion object (an object that has Lambertian characteristics as reflection characteristics), the image of the diffusion object is captured with incident light from various directions being mixed. In the present embodiment, with respect to the light emission region of the illumination device 3, the emission intensities of the three light components (RGB) are varied respectively in directions at equal angular differences (120 degrees) as shown in FIG. 2, and the degree of variation in the three light components is set to be equal. Accordingly, as shown in FIG. 9, with respect to any zenith angle, the total light intensity per color from all azimuth angle directions at the zenith angle is the same for all colors. Even if integration is performed for all zenith angles, the total light intensity is the same for all colors. Therefore, the RGB light components that are incident on the camera, which is positioned in the vertical direction from the diffusion object, have the same intensity, and the captured image of the diffusion object is obtained by capturing reflection light of white light. That is, in the case where an image capturing target is formed by both a specular object (measurement target object) and a diffusion object, it is possible to measure the surface shape of the specular object, and at the same time, to perform image capturing of the diffusion object as if it were irradiated with white light. Accordingly, for example, when soldering inspection is performed, it is possible to inspect inspection targets other than solder (substrate, IC, or the like) based on the relevant colors.

Figure 10:
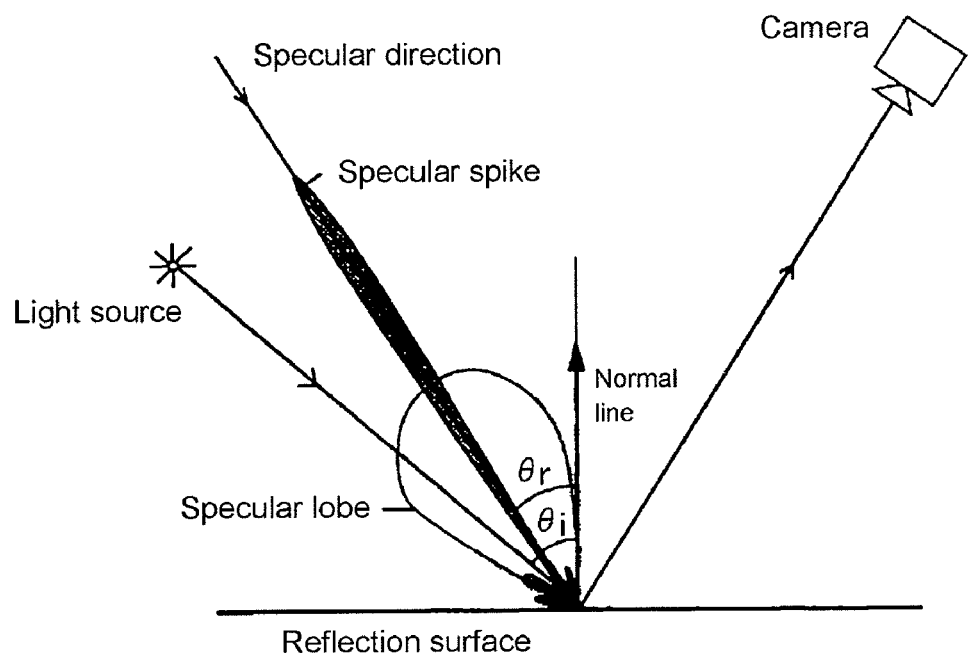
FIG. 10 is a diagram illustrating reflection characteristics.

Also, by using the above-described illumination device 3, it is possible to perform accurate measurement of even a target object having uneven reflection characteristics. This will be described below. As shown in FIG. 10, the reflection light of light that is incident on an object that does not have a perfectly specular surface consists of two types of light, namely, sharp and narrow light in a specular direction (specular spike) and dim and spread light in a direction deviated from the specular direction (specular lobe). "Specular lobe" means spreading of specular reflection light caused by minute recesses/protrusions (microfacets) on the measurement target surface. As the variation in the orientations of the microfacets is larger, that is, as the surface is rougher, the specular lobe spreads more. In contrast, as the variation in the orientations of the microfacets is smaller, the object comes closer to the condition of a perfectly specular surface. Here, the reflection characteristics are represented by the deviation (angle) from the specular direction and the ratio of the light intensity of the lobe to that of the spike. With an object having uneven reflection characteristics, the shape of the specular lobe differs depending on the surface roughness at each position on the surface. When the surface is very rough, reflection light is formed by the specular lobe only. The ratio between the specular lobe and the specular spike becomes close to 1, and the distinction of the two becomes difficult.

Due to such spreading of the specular lobe, the luminance value of the captured image is affected not only by light from the light emission region (the region R in FIG. 4) corresponding to the position on the object surface, but also by light from the region around the light emission region. That is, with an object having a rough surface, light from the light emission region corresponding to the specular direction and light from the region around the light emission region are mixed, and a spectrum characteristic different from that of the perfectly specular surface is observed.

At this time, if illumination could be performed such that light beams coming from surrounding regions cancel each other so as to maintain a spectrum characteristic similar to that of the perfectly specular surface, then even with an object having uneven reflection characteristics or an object having a rough surface, a measurement could be performed as if it were an object having a perfectly specular surface. In order to realize this, theoretically, it is sufficient if the light source distribution (illumination pattern) of the illumination device 3 is set as described below.

Figure 11:
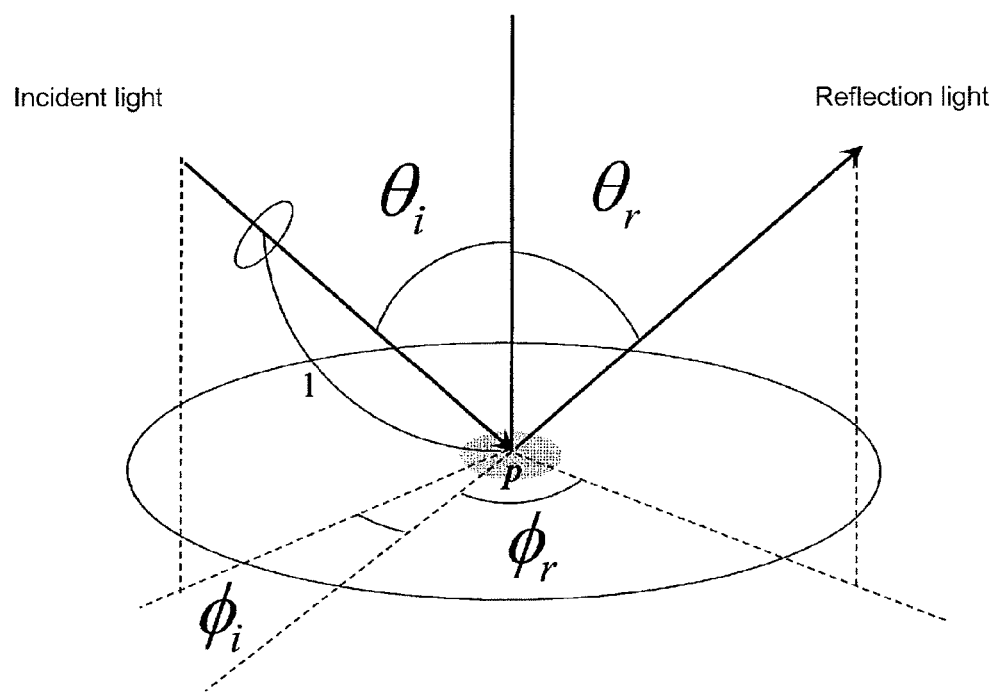
FIG. 11 is a diagram illustrating incident light and reflection light.

That is, as shown in FIG. 11, when Li (p, θi, φi) is the radiance of light from the light source that is incident on a measurement point p from the direction of an incident angle (θi, φi), it is sufficient if the expression indicated below is satisfied with respect to any normal vector at a point p and any point-symmetrical region Ω on the light emission region.

$$\iint_\Omega L_i(p,\theta_i,\phi_i) \cdot f(p,\theta_i,\phi_i,\theta_r,\phi_r) \sin\theta_i d\theta_i d\phi_i = k_f L_i(p,\theta_r,\phi_r)$$ [Expression 1]

In Expression 1, p indicates a measurement point on the object surface, (θi, θi) indicates an incident direction of the light source (θ indicates the zenith angle component, and φ indicates the azimuth angle component. The same will be applicable to the description thereafter), (θr, φr) indicates a reflection direction (the direction of the line of sight of the camera) of light from the light source, f indicates reflection characteristics at the point p, Ω indicates an apparent solid angle of the specular lobe with the reflection characteristics f, kf indicates a radiance attenuation ratio (depends on the reflection characteristics of the object surface).

With the illumination device 3 of the present embodiment, the emission intensity of each of the RGB light components is set so as to vary linearly with respect to the angle (longitude) (see FIGS. 2 and 3). An illumination pattern in which the luminance varies linearly with respect to the angle (longitude) is one approximate solution of Expression 1. Also, an illumination pattern of the illumination device 3 obtained by mutually overlaying patterns of the RGB light components is also an approximate solutions of Expression 1.

Figure 12:
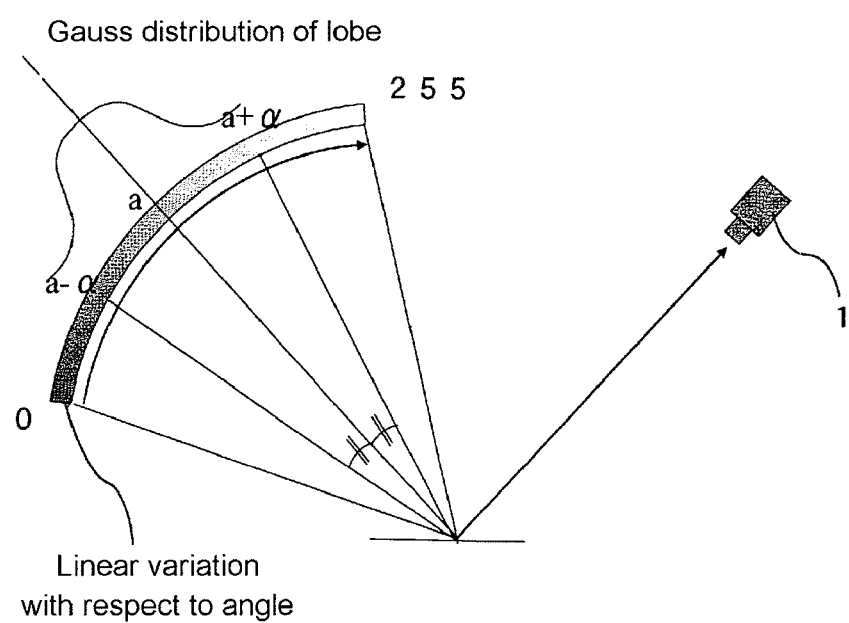
FIG. 12 is a diagram illustrating an offset effect of specular lobe.

The fact that it is possible to offset an effect of the specular lobe by using such an illumination pattern will be described with reference to FIG. 12 from another point of view. FIG. 12 shows a one-dimensional direction of the luminance variation by which substantially ideal light can be obtained, in order to describe an effect of the illumination pattern of the present embodiment. Here, as shown in FIG. 12, only light from three points, namely, light at an angle a (specular direction), an angle (a+α), and an angle (a−α) is considered. The lobe coefficients of the light from the positions at the angle (a+α) and the angle (a−α) are assumed to be equal, which is σ. Also, the emission intensity of the illumination device 3 is assumed to be in proportion to the angle, and the emission intensities at the positions at the angle (a−α), a, and (a+α) are assumed to be (a−α)L, aL, and (a+α)L, respectively. Then, the combined reflection light from the three points is obtained with the following equation; σ(a−α)L+aL+σ(a+α)L=(1+2σ)aL, and thus the effect of diffusion light from surrounding regions are offset. Note that although only two points at the angles (a±α) are considered in this example, it is easily understood that all effects of diffusion light from surrounding regions are offset. This is true for each of the RGB light components, and accordingly, the characteristic amount represented by the emission intensity ratio among the RGB colors has the same value as in the case of perfectly specular reflection. Therefore, even for an object having uneven reflection characteristics, as in the case of perfectly specular reflection, it is possible to accurately obtain the surface shape of the measurement target object based on a single captured image.

Note that the above description is given with respect to the direction in which the most ideal effect is obtained. With other directions, linearity as described above cannot be completely achieved, and thus an effect of diffuse reflection cannot be offset in a strict sense, but it is possible to remove an effect of diffuse reflection to the extent that there is no practical problem. Although the above embodiment relates to measurement of a specular object, the present invention can be applied to measurement of a diffusion object. For measuring a normal line on a diffusion object, a "shape from shading" technique, for which photometric stereo is an example, is known. "Shape from shading" is a technique in which the shape of an object is obtained based on the brightness of ifs surface, by making use of the property that as the inclination (normal line) of the surface of a diffusion object deviates from the light source direction, brightness is reduced. In such techniques, as in the embodiment with a specular object described above, the correspondence relation between the normal line on the object and the brightness of the surface is obtained in advance based on an image captured by projecting measurement illumination on a model object whose surface shape is known (a sphere is used in many cases). Similar to a specular object, when the positional relation with the light source is changed due to the position of the model object and the inspection position being different, the relation between the brightness and the normal line cannot be maintained, and an error occurs. As the distance between the position of the model object and the measurement position increases, the error is greater, which is the same as the case of a specular object. Accordingly, also on the diffusion surface, by performing measurement while changing the correspondence relation for each position based on reference positions in a plurality of fields of view according to the present invention, it is possible to suppress worsening of accuracy in the normal line calculation in an entire image as much as possible.

Variation of Illumination Device

Figure 13A:
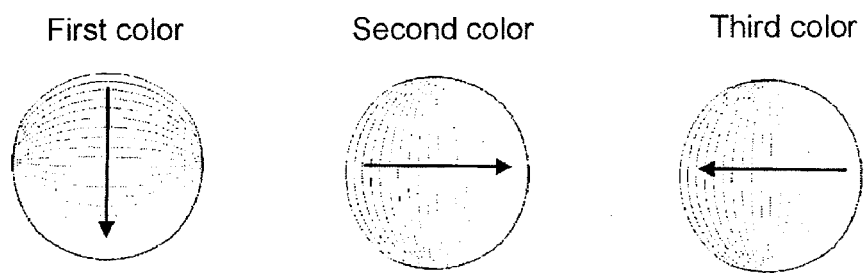
FIG. 13 is a diagram illustrating modified examples of illumination patterns.
Figure 13B:
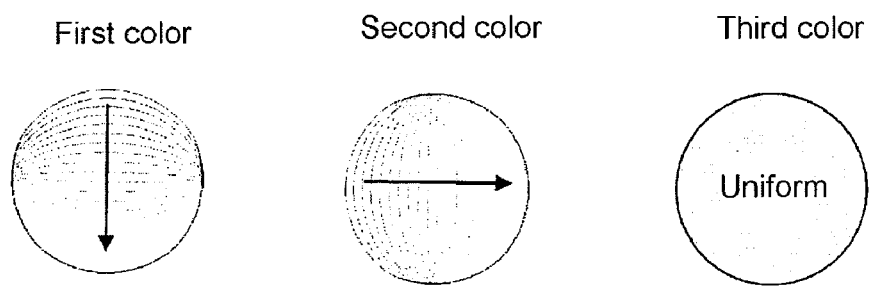

In the description of the embodiment described above, an illumination device is used in which patterns of three colors, RGB, in each of which the emission intensity varies with the angle, the variation directions defining angles of 120 degrees, are mutually overlaid. However, the illumination pattern is not limited thereto. For example, an illumination pattern may be used which is formed by combining patterns in which the emission intensity varies in mutually different directions, for example, patterns of three colors in which the emission intensity varies in a downward direction, right direction, and left direction, respectively, as shown in FIG. 13A. Also, the emission intensity need not be varied with the angle for all of the three colors, and as shown in FIG. 13B, an illumination pattern may be used in which for one color, light is emitted at an uniform luminance from the entire surface, and for two other colors, patterns are used in which the emission intensity varies with the angle in mutually different directions.

Figure 13C:
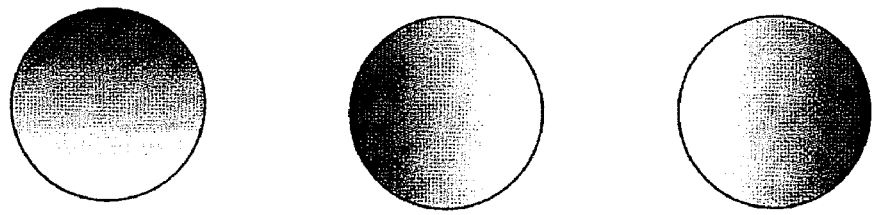

Also, in the embodiment described above, an illumination device is used in which illumination patterns of different color channels are mutually overlaid, thereby enabling to restore the three-dimensional shape of a target object with a single measurement (illumination and image capturing). Note that two or more types of illumination patterns may be sequentially turned on to perform image capturing, and the three-dimensional shape may be restored by using a plurality of obtained images, although in this case the required measurement time is longer than the embodiment described above. The same restoration results can be obtained by this method as well. Note that when image capturing is performed while the illumination patterns are switched, a plurality of monochrome illumination patterns having mutually different emission intensity distributions may be used (in this case, a monochrome camera may be used), as shown in FIG. 13C.

Figure 14A:
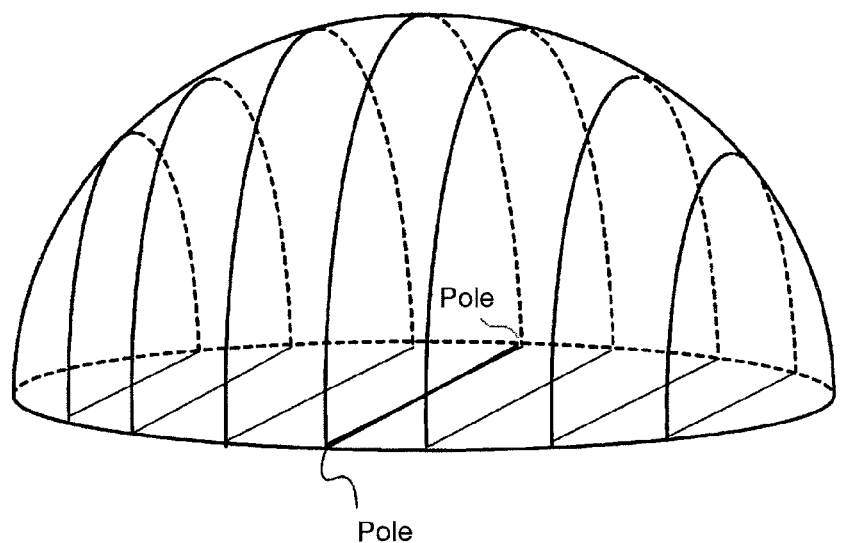
FIG. 14 is a diagram illustrating a modified example of the illumination pattern.
Figure 14B:
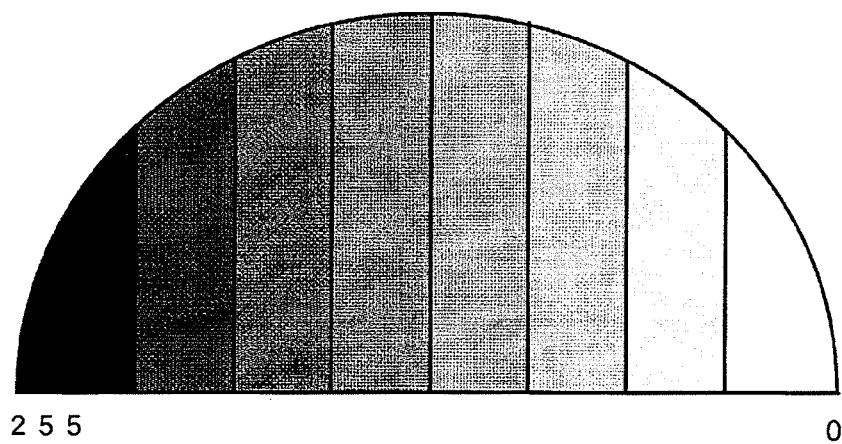

In the embodiment described above, although an illumination pattern in which the emission intensity varies linearly with respect to the angle in the longitude direction is used, the illumination pattern is not limited thereto. For example, as shown in FIG. 14, it is suitable to use an illumination pattern in which the emission intensity varies linearly with respect to the latitude direction. Such an illumination pattern is also one of the approximate solutions of Expression 1, and it becomes possible to detect regular reflection light by offsetting substantially all effects of the specular lobe.

Figure 15:
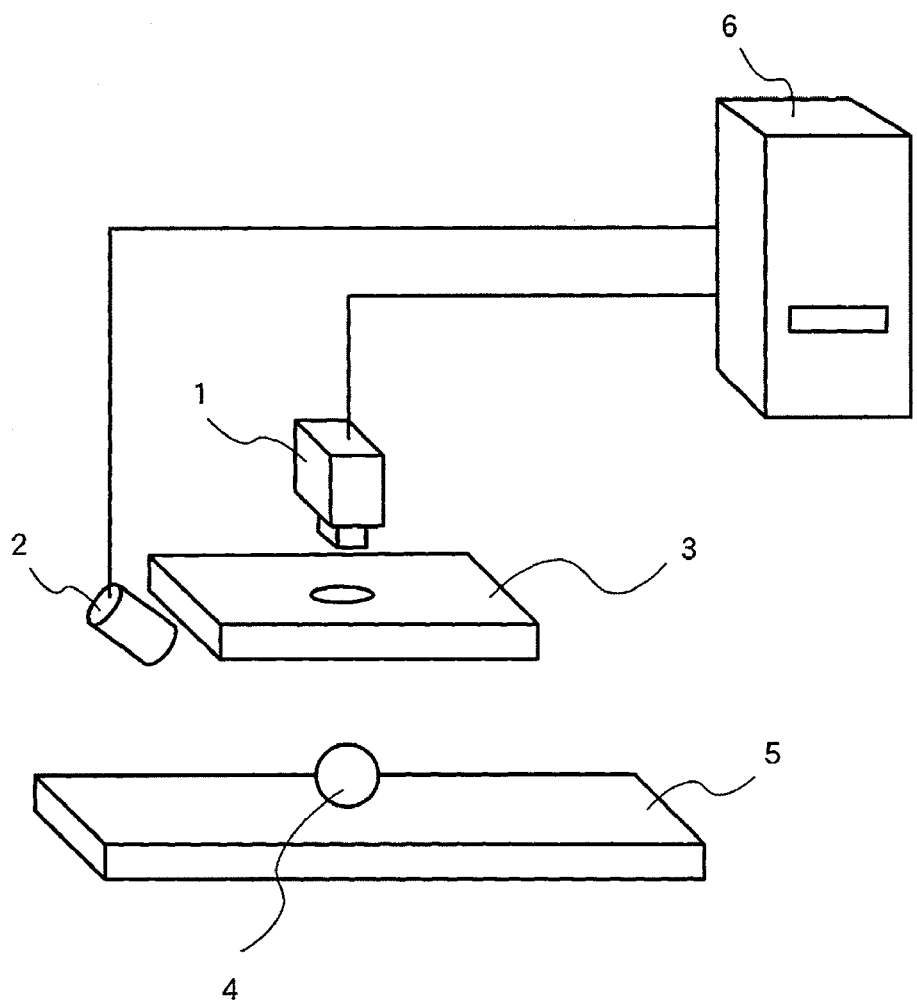
FIG. 15 is a diagram illustrating the configuration of a shape measurement apparatus including a plate-shaped illumination device.

Also, the shape of the illumination device 3 is not limited to a dome shape (hemispherical shape), and may be a plate shape as shown in FIG. 15. Also, the illumination device 3 may have a shape formed by curving a plate into an arc shape. To restore the shape, any illumination can be used with which the position of the light source can be uniquely obtained based on the observed image.

Figure 16A:
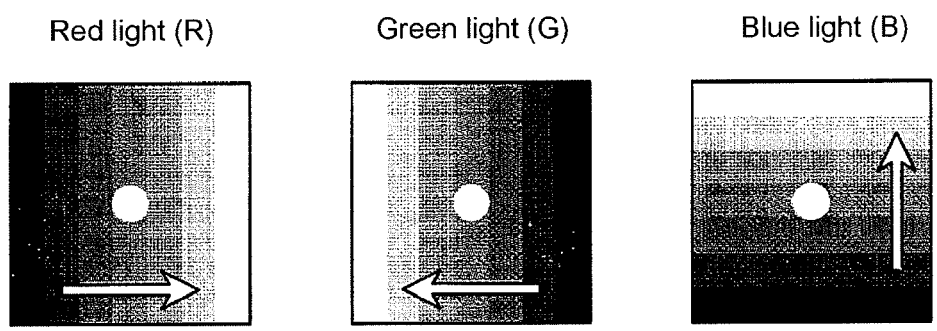
FIG. 16 is a diagram illustrating illumination patterns for the plate-shaped illumination device.
Figure 16B:
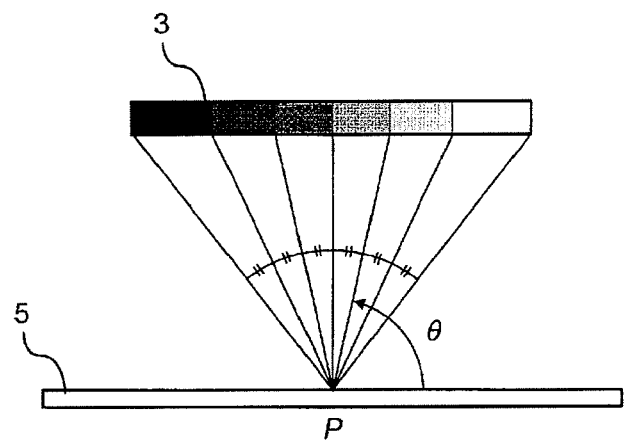

Also, as an example shown in FIG. 16A, a red (R) light pattern in which the emission intensity increases to the right direction, a green (G) light pattern in which the emission intensity increases to the left direction, and a blue (B) light pattern in which the emission intensity increases to the upper direction, may be mutually overlaid. In this case as well, as shown in FIG. 16B, by linearly varying the emission intensity with respect to the angle θ in each pattern, substantially all effects of the specular lobe can be offset. Here, θ is an angle around the straight line that passes through the point P (point at which the measurement target object is disposed) and is parallel to the measurement stage 5. Alternatively, θ can be expressed as an angle formed by the plane that passes through the line of equal emission intensity (isochromatic line) on the light emission region of the illumination device 3 and the point P, and the plane parallel to the measurement stage 5.

Other Variations

The present invention is not limited to the shape measurement apparatus of the embodiment described above, and can be preferably applied to any type of shape measurement apparatus, as long as the shape measurement apparatus uses a table in which characteristic amounts (color or brightness) of the image are associated with normal lines (or light source angles).

1: camera, 3: illumination device, 4: measurement target object, 5: measurement stage, 6: information processing apparatus, H: inspection head

What is claimed is:

1. A shape measurement apparatus comprising:
    an illuminator that irradiates light onto a measurement target object disposed on a stage;
    an image capturing unit that captures an image of the measurement target object;
    a characteristic amount calculator, that calculates a characteristic amount corresponding to at least one of a color and brightness of a plurality of points of interest on a surface of the measurement target object, based on an image of the measurement target object obtained by the image capturing unit in a state in which light is emitted from the illuminator;
    a storage unit that stores predetermined data that associates a value of the characteristic amount with information that specifies an orientation of a normal line on the surface based on the characteristic amount value; and
    a shape calculator that calculates orientations of normal lines at the plurality of points of interest, based on the values of the characteristic amount calculated by the characteristic amount calculator, by referencing the predetermined data stored in the storage unit, and calculates a three-dimensional shape of the surface of the measurement target object based on a result of the calculated orientations,
    wherein the storage unit stores a plurality of data sets generated, respectively, for a plurality of reference positions arranged in a field of view of the image capturing unit, and
    the shape calculator selects the data set to be referenced based upon a position of a point of interest.

2. The shape measurement apparatus according to claim 1, wherein the field of view of the image capturing unit is divided into a plurality of sub-regions such that each sub-region includes a reference position, each sub-region is associated with one data set, and wherein, as the data set to be referenced, the shape calculator selects the data set that corresponds to a sub-region to which the point of interest belongs.

3. The shape measurement apparatus according to claim 1, wherein each of the plurality of data sets is generated based upon an image of a model object whose surface shape is known, the image of the model object being obtained by disposing the model object at the reference position and capturing the image of the model object with the image capturing unit in a state in which light is emitted from the illuminator.

4. The shape measurement apparatus according to claim 2, wherein each of the plurality of data sets is generated based upon an image of a model object whose surface shape is known, the image being obtained by disposing the model object at the reference position and capturing the image of the model object with the image capturing unit in a state in which light is emitted from the illuminator.

5. The shape measurement apparatus according to claim 1, wherein the illuminator is a surface light source that has a light emission region having a predetermined area, and wherein the spectral distributions of light that is emitted from different positions in the light emission region are different from each other.

6. The shape measurement apparatus according to claim 1, wherein the illuminator is a surface light source that emits light formed by overlaying a plurality of illumination patterns that have different emission intensity distributions, or that sequentially emits said plurality of illumination patterns, the emission intensity distribution of each illumination pattern being set such that the emission intensity varies linearly with respect to an angle defined between a first plane and a second plane, the first plane passing through both a line of equal emission intensity on a light emission region of the surface light source and a point at which the measurement target object is positioned and the second plane extending parallel to the stage.

7. A calibration method of a shape measurement apparatus that irradiates light onto a measurement target object with an illumination device, captures an image of the measurement target object by an image capturing device in a state in which light is emitted, and calculates a three-dimensional shape of a surface of the measurement target object based on a characteristic amount relating to at least one of a color and brightness, obtained for a plurality of points of interest on the surface of the measurement target object, of the captured image, the calibration method comprising:
- positioning a model object, whose surface inclination is known, in a field of view of the image capturing device, irradiating the model object with the illumination device by emitting light from at least a plurality of different directions, the emission intensity distributions of the light from the different directions being different from each other;
- extracting a characteristic amount with respect to an inclination of the surface of the model object based on the captured image; and
- storing data associating a position on the image at which the model object is positioned with the extracted characteristic amount as data for calibration of measurement values at a plurality of measurement positions of the measurement target object.

8. The calibration method according to claim 7, further comprising providing the model object, whose surface inclination is known, as a specular hemispherical body.

9. The calibration method according to claim 7, further comprising capturing an image of the model object from above the model object with the image capturing device.

10. The calibration method according to claim 7, further comprising providing the illumination device as a surface light source that has a light emission region having a predetermined area and irradiates the model object with light from a plurality of positions in the light emission region, and providing the spectral distributions of the light from the different positions in the light emission region to be different from each other.

11. The calibration method according to claim 7, further comprising providing the illumination device as a surface light source that has a light emission region capable of irradiation by overlaying a plurality of illumination light patterns that have different emission intensity distributions from each other or sequential irradiation by the plurality of illumination light patterns, and providing the illumination device to irradiate the model object with light having different emission intensity distributions from each other, the emission intensity distribution of the patterns being provided such that the emission intensity varies linearly with respect to an angle defined between a first plane and a second plane, the first plane passing through both a line of equal emission intensity on a light emission region of the surface light source and a reference position at which the object is positioned and the second plane extending to a plane on which the model object is positioned.

* * * * *